US010859223B2

United States Patent
Crawford

(10) Patent No.: US 10,859,223 B2
(45) Date of Patent: Dec. 8, 2020

(54) FLOATING CANDLE OVER A BASE WITH SUSPENDED DECORATION

(71) Applicant: Eldolgina Crawford, Orlando, FL (US)

(72) Inventor: Eldolgina Crawford, Orlando, FL (US)

(*) Notice: Subject to any disclaimer, the term of this patent is extended or adjusted under 35 U.S.C. 154(b) by 131 days.

(21) Appl. No.: 15/917,623

(22) Filed: Mar. 10, 2018

(65) Prior Publication Data
US 2018/0259145 A1    Sep. 13, 2018

Related U.S. Application Data

(60) Provisional application No. 62/470,136, filed on Mar. 10, 2017.

(51) Int. Cl.
| | |
|---|---|
| *F21S 13/12* | (2006.01) |
| *F21V 35/00* | (2006.01) |
| *C11C 5/00* | (2006.01) |
| *A61L 9/04* | (2006.01) |
| *A61L 9/03* | (2006.01) |
| *A61L 9/12* | (2006.01) |
| *F21W 121/00* | (2006.01) |

(52) U.S. Cl.
CPC .............. *F21S 13/12* (2013.01); *A61L 9/03* (2013.01); *A61L 9/048* (2013.01); *A61L 9/12* (2013.01); *C11C 5/004* (2013.01); *C11C 5/006* (2013.01); *C11C 5/008* (2013.01); *F21V 35/00* (2013.01); *A61L 2209/12* (2013.01); *F21W 2121/00* (2013.01)

(58) Field of Classification Search
CPC ............ C11C 5/008; F21S 13/12; F21V 35/00
See application file for complete search history.

(56) References Cited

U.S. PATENT DOCUMENTS

| 4,427,366 A * | 1/1984 | Moore ................ A61L 9/03 422/126 |
| 4,894,008 A * | 1/1990 | Lee .................. F21V 35/00 431/290 |
| 5,395,233 A * | 3/1995 | Karp ................ C11C 5/002 431/126 |
| 5,951,278 A * | 9/1999 | Young ................ F21V 5/00 362/161 |
| 6,033,210 A * | 3/2000 | Freeman ............. C11C 5/002 362/161 |
| 6,210,153 B1 * | 4/2001 | Freeman ............. C11C 5/008 264/271.1 |

(Continued)

*Primary Examiner* — Avinash A Savani
*Assistant Examiner* — Deepak A Deean
(74) *Attorney, Agent, or Firm* — Wilson Dutra, PLLC; Camille A. Wilson

(57) ABSTRACT

The present disclosure relates to a new way to manufacture and incorporate decorative features within a candle using a floating candle and a suspension base. The present disclosure describes a floating candle that may be located over a base with suspended decoration. In some aspects, the floating candle may comprise an ignitable wick that may extinguish prior to reaching the base. In some implementations, the base may comprise a liquid that may allow for movement of the decorations within the base. In some aspects, the base may comprise a rigid material, such as a hardened epoxy or polymerized monomer, wherein the curing of the material may occur after the decorations may be placed in the base.

14 Claims, 5 Drawing Sheets

(56) References Cited

U.S. PATENT DOCUMENTS

| | | | | |
|---|---|---|---|---|
| 6,241,512 B1 * | 6/2001 | Freeman | ............... | C11C 5/002 |
| | | | | 431/291 |
| 6,435,694 B1 * | 8/2002 | Bell | ............... | C11C 5/008 |
| | | | | 362/161 |
| 6,454,561 B1 * | 9/2002 | Colthar | ............... | C11C 5/006 |
| | | | | 425/803 |
| 6,474,980 B2 * | 11/2002 | LaVanier | ............... | F21S 13/12 |
| | | | | 431/126 |
| 6,491,517 B2 * | 12/2002 | Freeman | ............... | C11C 5/008 |
| | | | | 362/161 |
| 6,669,468 B2 * | 12/2003 | Pesu | ............... | F21V 1/22 |
| | | | | 431/125 |
| 6,716,026 B1 * | 4/2004 | Beougher | ............... | F21V 35/00 |
| | | | | 431/290 |
| 7,232,550 B1 * | 6/2007 | Rodgers | ............... | A61L 9/03 |
| | | | | 422/125 |
| D750,814 S * | 3/2016 | Moyal | ............... | D26/22 |
| D767,800 S * | 9/2016 | Moyal | ............... | D26/22 |
| D787,096 S * | 5/2017 | Moyal | ............... | D26/22 |
| D825,790 S * | 8/2018 | Moyal | ............... | D26/6 |
| 2007/0134606 A1 * | 6/2007 | Lin | ............... | C11C 5/008 |
| | | | | 431/291 |
| 2015/0128391 A1 * | 5/2015 | Lynch | ............... | A61G 17/08 |
| | | | | 27/1 |
| 2016/0131359 A1 * | 5/2016 | Trew | ............... | F21V 35/00 |
| | | | | 431/289 |

* cited by examiner

FLOATING CANDLE OVER A BASE WITH SUSPENDED DECORATION

CROSS-REFERENCE TO RELATED APPLICATION

This application claims priority to and the full benefit of U.S. Provisional Patent Application Ser. No. 62/470,136, filed Mar. 10, 2017, and titled "FLOATING CANDLE OVER A BASE WITH SUSPENDED DECORATION", the entire contents of which are incorporated in this application by reference.

BACKGROUND OF THE DISCLOSURE

Candles have a rich creation history, with multiple civilizations leaving their unique mark on how different iterations were made. Candles proliferated when olive oil became scarce for use with oil lamps. Egyptians used rush lights or torches by soaking the pithy core of reeds in melted animal fat. Romans developed dipped candles from tallow, which is credited for the first use of a wick. Early Chinese civilizations created candles from whale fat or beeswax. Indians boiled cinnamon and used the resulting wax for candles. Tibetans created candles with yak butter. Tallow became the standard candle material in Europe, but produced a disagreeable aroma due to the glycerin contained in the candles. Beeswax eventually replaced tallow, but were reserved for formal settings due to their expense.

Over time, more materials were discovered and used for candle making. The expansion of the whaling industry led to the discovery that spermaceti oil could be used for candles. Spermaceti produced a brighter light and did not soften or bend in summer heat, leading to the first mass market candle. Eventually colza oil was used to produce candles that had clear, smokeless flames. French chemists created stearin, a hardening agent used in soap as well as candles. At this point, innovations started to focus on mass producing candles, though innovations involving wicks and other oils were discovered as well.

Though candles were initially used for the light they provided, they are also used for the scents they can produce. Based on the history of the candle, the candle's body typically contains a solid fuel source, such as paraffin wax. A wick runs through the candle's body from the body and is exposed through the top. The wick acts as a fuel pump when a candle is burning and is usually made of cotton fibers that have been braided together.

The candles industry began to decline when superior lighting became mainstream, such as kerosene lamps and the invention of the incandescent light bulb. The light bulb itself was a safer invention to provide lighting in the home.

Today, candles predominantly serve a decorative function. Companies sell scented candles in a variety of colors, shapes, and sizes. Candles can be found in a variety of types, such as a taper, a pillar, a column, a container, and a votive. The candle industry is focuses on creating unique wax blends, aiming to deliver unique fragrances while also providing long burn times.

SUMMARY OF THE DISCLOSURE

What is needed is a process and method of setting, preserving, and enhancing the decorative features of certain candles that can be used in a variety of waxes, gels, and oils. This allows for a clear design within the candle while burning the top without destroying a design. A process for preserving these decorative features in transportation will also be needed to ensure that they maintain these enhancements.

Accordingly, the present disclosure relates to a candle with a decorative base. More specifically, the present disclosure describes a floating candle that may float over a base with suspended decoration. In some aspects, the floating candle may comprise an ignitable wick. In some embodiments, the ignitable wick may extinguish prior to reaching the base. In some implementations, the base may comprise a liquid that may allow for movement of the decorations within the base. In some aspects, the base may comprise a rigid material, such as a hardened epoxy or polymerized monomer, wherein the curing of the material may occur after the decorations may be placed in the base.

According to the present disclosure, in some aspects, a floating candle device may comprise a suspended decoration; a suspension base comprising at least one suspension composition configured to house the suspended decoration; a floating candle located within the suspension base and above the suspension base; a container configured to house the suspended decoration, the suspension base, and the floating candle. In some aspects, the suspended decoration may be anchored to the container. In some embodiments, the suspended decoration may float within the suspension base.

In some implementations, the suspended decoration may comprise a first portion and a second portion, wherein the first portion may float within the suspension base and the second portion may be anchored to the container. In some embodiments, a light mechanism may be configured to illuminate one or more the suspension base, the suspended decoration, the floating candle, or the container. In some aspects, the suspension composition may comprise a solid. In some implementations, the suspension composition may comprise a fluid.

In some aspects, the candle material may comprise a gel. In some embodiments, the suspension composition may comprise a gel or fluid. In some implementations, the suspension composition may comprise a solid.

In some embodiments, a surface decoration may be located on a surface of the container. In some aspects, one or both the floating candle or the suspension base may comprise one or more colors. In some embodiments, one or both the floating candle or the suspension base comprises one or more fragrances. In some implementations, the floating candle may be replaceable.

In some aspects, a barrier layer may be located between the suspension base and the floating candle. In some embodiments, the suspended decoration may comprise a first portion and a second portion, wherein the first portion may float within the suspension base and the second portion may be anchored to one or both the container or the barrier layer.

In some implementations, the floating candle may comprise a wick; a wick base configured to anchor the wick within the floating candle; and a candle material configured to melt as the wick burns. In some aspects, the wick base may be anchored in the candle material. In some embodiments, the wick base may be anchored in the barrier layer. In some implementations, the wick base may be anchored in the suspension base.

BRIEF DESCRIPTION OF THE DRAWINGS

The accompanying drawings, that are incorporated in and constitute a part of this specification, illustrate several embodiments of the disclosure and, together with the description, serve to explain the principles of the disclosure.

DETAILED DESCRIPTION

The present disclosure provides generally for a new way to manufacture and incorporate decorative features within a candle using a floating candle and a suspension base. According to the present disclosure, there are a variety of methods on how to create, treat, prepare, and set floating candles, decorative features, and suspension bases.

More specifically, the present disclosure describes a floating candle that may float over a base with suspended decoration. In some aspects, the floating candle may comprise an ignitable wick. In some embodiments, the ignitable wick may extinguish prior to reaching the base. In some implementations, the base may comprise a liquid that may allow for movement of the decorations within the base. In some aspects, the base may comprise a rigid material, such as a hardened epoxy or polymerized monomer, wherein the curing of the material may occur after the decorations may be placed in the base.

In the following sections, detailed descriptions of examples and methods of the disclosure will be given. The description of both preferred and alternative examples, though thorough, are exemplary only, and it is understood that to those skilled in the art variations, modifications, and alterations may be apparent. It is therefore to be understood that the examples do not limit the broadness of the aspects of the underlying disclosure as defined by the claims.

Glossary

Floating Candle: as used herein refers to a functional layer over a suspension base. The term candle is used for simplicity and may actually include functionality that may not require or allow for the burning of any portion of the candle. For example, a candle may include an air freshener that may release fragrance without burning.

Suspension Base: as used herein refers to an at least partially transparent base comprising a decorative feature suspended in a base material, wherein a floating candle appears to float over the suspension base. In some aspects, a suspension base may comprise one or more suspension compositions, such as a fluid, gel, or solid, as nonlimiting examples. In some embodiments, the floating candle may actually float over the suspension base. In some aspects, the suspension base may comprise a rigid material that may hold the floating candle. In some implementations, a barrier layer may separate the suspension base and the floating candle.

Figure 1:
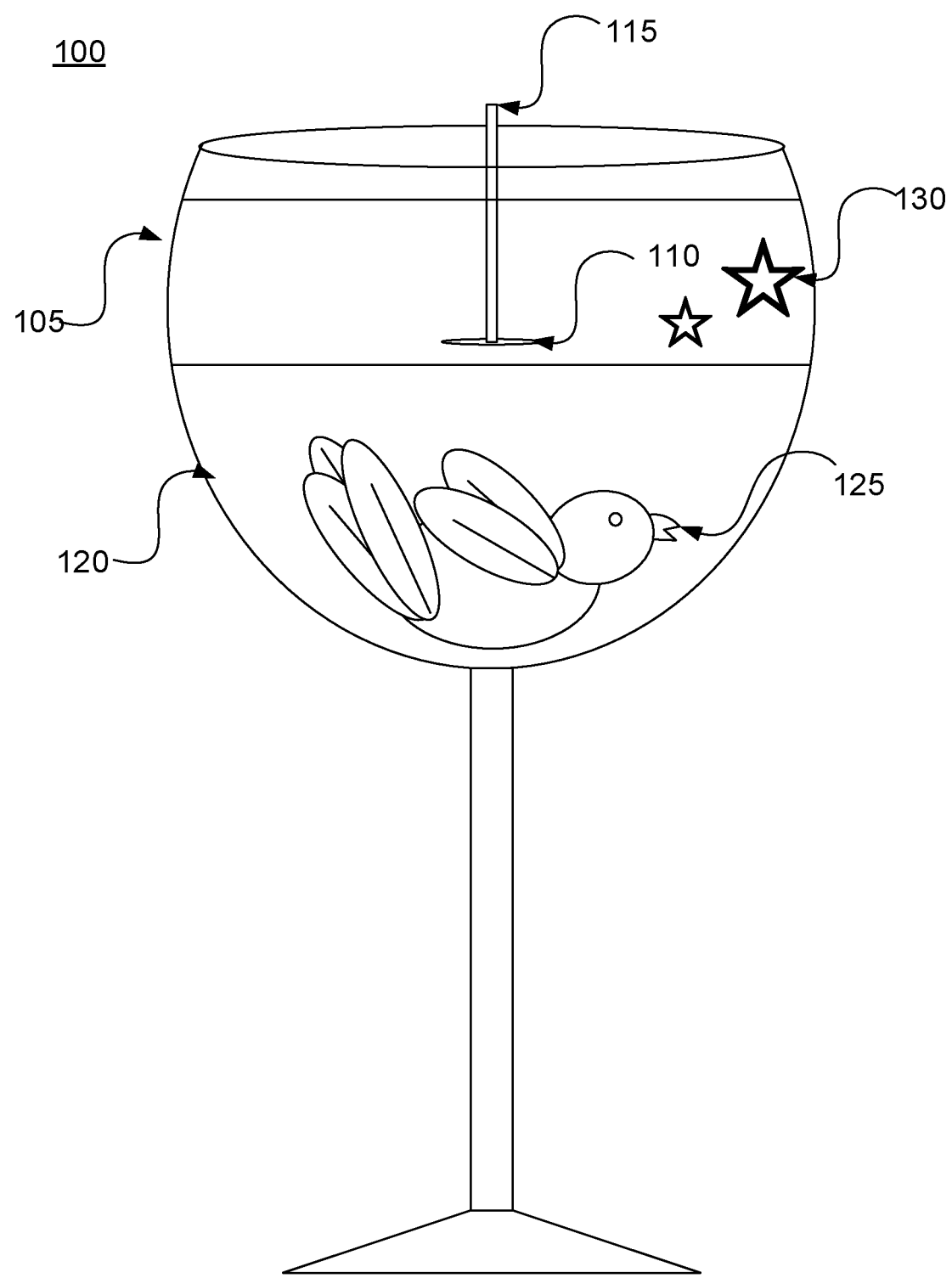
FIG. 1 illustrates an exemplary embodiment of a floating candle in a stemmed container with static suspended decoration.

Referring now to FIG. 1, an exemplary embodiment of a floating candle 105 in a stemmed container 100 with static suspended decoration 125 is illustrated. In some embodiments, a suspended base 120 may comprise a transparent material, wherein decorations suspended within the suspended base 120 may be visible. In some aspects, the suspended base 120 may comprise a static suspended decoration 125, wherein the movement of the static suspended decoration 125 is limited. In some implementations, the suspended base 120 may comprise a rigid material, wherein any suspended decoration may be static.

In some embodiments, the suspended base 120 may comprise a fluid, and the static suspended decoration 125 may be pretreated and anchored to at least a portion of the stemmed container 100. For example, as illustrated, the static suspended decoration 125 may comprise a bird with feathers, wherein a water-resistant, hardening coating may encapsulate the static suspended decoration 125, wherein the movement of the feathers and any other loose features may be limited. In some implementations, the stemmed container 100 may further comprise exterior decorations 130, such as through use of adhesives, paints, or other decorative techniques.

In some aspects, the floating candle 105 may sit on top of the suspended base 120, such as where the candle material may be more buoyant than the material of the suspended base 120. In some embodiments, the floating may occur during production, and the materials may harden, such as through cooling or curing. In some aspects, the floating candle 105 may comprise a wick 115 with wick base 110 that may anchor the wick 115 within the floating candle. In some embodiments, the wick base 110 may be anchored at a predefined distance from the suspended base 120, which may limit the heat exposure of the suspended base 120.

In some embodiments, the floating candle 105 may comprise a material common to candles, such as a wax, gel, or resin. The wax may comprise beeswax, microcrystalline wax, paraffin wax, palm wax, or other plant wax, as non-limiting examples. A gel may comprise a mixture of polymer and mineral oil. The material of the floating candle 105 may vary based on aesthetic preferences, burn rate, melting point, buoyancy, or density relative to the suspended base, luminous intensity, or other characteristics, as non-limiting examples.

For example, if the purpose of the floating candle 105 is to provide long-lasting light and fragrance, a slow-burning wax with perfume may be preferable. As another example, if the purpose of the floating candle 105 is to reveal a gender of a baby during a baby shower, a quick-burning gel with opaque color may be preferable so that the reveal may occur within a few hours or less. In some aspects, multiple materials may be used for the floating candle, wherein each material may provide a unique functionality. For example, a clear, scented gel may form a portion of the floating candle 105 with an opaque, paraffin core, wherein the wick 115 may burn the paraffin core. In some embodiments, the paraffin core may be replaceable, potentially extending the functionality of the floating candle 105.

In some implementations, a floating candle and suspension base may be situated within a variety of housings, such as glass, plastic, or metal. In some aspects, a floating candle and suspension base may be placed in a variety of shapes, such as a cube, square, cylinder, sphere, cone, or pyramid. In some aspects, the housing may comprise a functional vessel, such as a wine glass or serving bowl. In some embodiments, the floating candle may be optional or removable, wherein the absence of the floating candle may allow for use of the housing according to its original function. For example, a wine glass may hold a consumable liquid over the suspended base. In some implementations, a housing may be used in conjunction with the suspension base for consumption. For example, a person may have a wine glass with a suspension base and use the wine glass as originally intended, with a suspension base also included.

Figure 2:
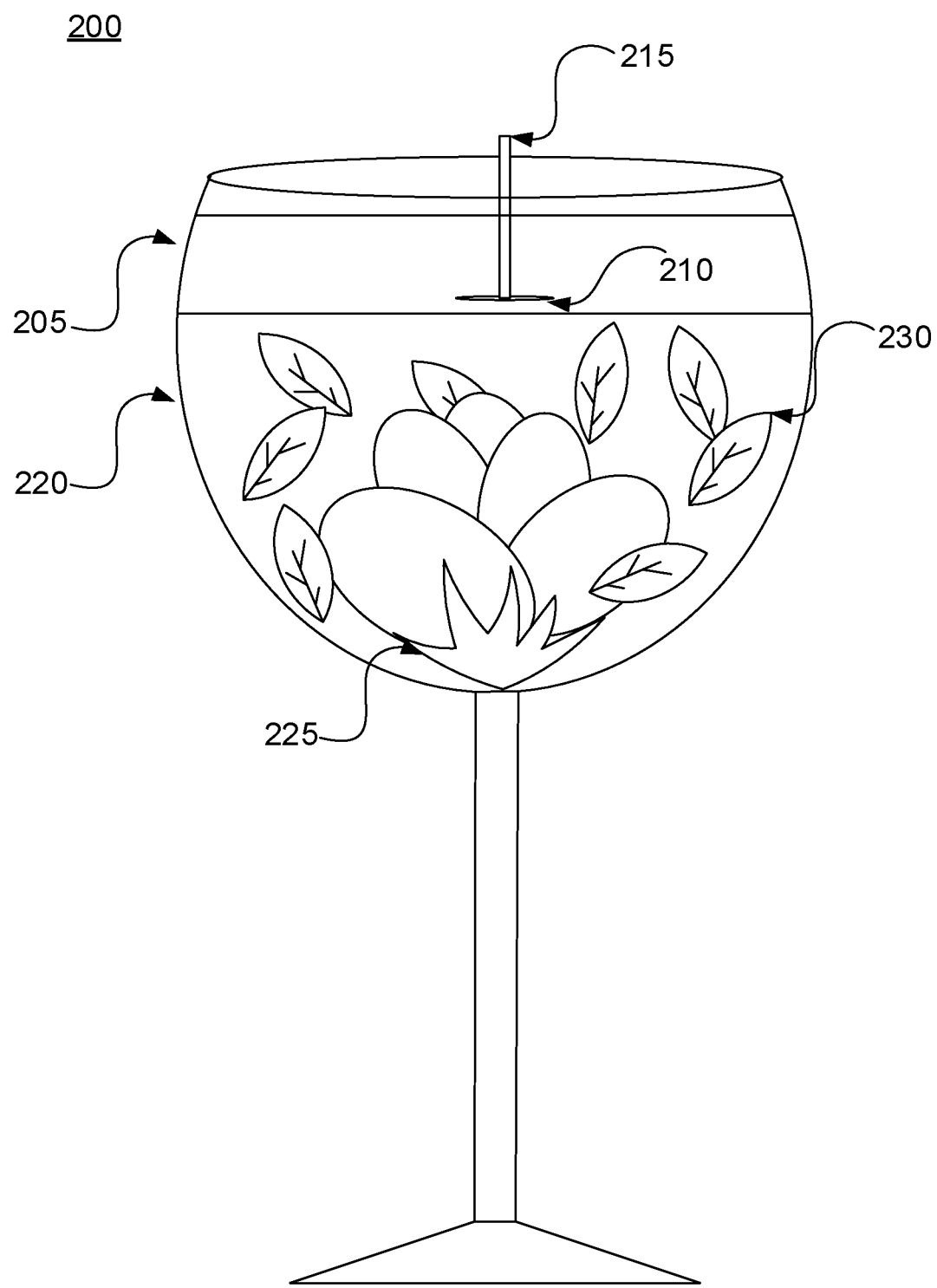
FIG. 2 illustrates an exemplary embodiment of a floating candle in a stemmed container with free-floating suspended decoration.

Referring now to FIG. 2, an exemplary embodiment of a floating candle 205 in a stemmed container 200 with free-floating suspended decoration 230 is illustrated. In some embodiments, the floating candle 205 may comprise a wick 215 anchored by a wick base 210. The suspension base 220 may comprise a fluid, wherein free-floating suspended decorations 230 may float and move when the stemmed container 200 is moved. In some aspects, free-floating suspended decorations 230 may be paired with static suspended decorations 225 to create a dynamic scene. For example, as illustrated, the static suspended decoration 225 may comprise a flower, and the free-floating suspended decorations 230 may comprise leaves, which may create a floral motif.

In some embodiments, the static suspended decoration 225 may comprise a photograph, and the free-floating suspended decorations 230 may comprise objects related to the photograph. For example, the photograph may be of a man who enjoys poker, and the floating suspended decorations 230 may be objects related to poker, such as chips and cards. Depending on the size of the stemmed container 200, the chips and cards may be an actual size or miniature versions.

In some aspects, the free-floating suspended decoration 230 may interact with the environment in the suspension base 220. In some embodiments, the free-floating suspended decoration 230 may move around to draw more attention to the static suspended decorations 225. For example, as described above, the free-floating suspended decorations 230 may revolve around the static suspended decoration 225 to accentuate the floral motif. In some implementations, a user may manipulate the suspension base 220 to initiate the interaction between the decorations, either physically, with a remote, or with a smart device.

For example, the free-floating suspended decoration 230 may comprise fake snow, and a user may manipulate the container 200 similarly to a snow globe. In some aspects, the floating candle 205 may be permanently attached to the container 200, which may allow a user to shake the container 200 without affecting the integrity of the system. In some embodiments, the floating candle 205 may be replaceable, which may extend the life or longevity of the system.

Figure 3:
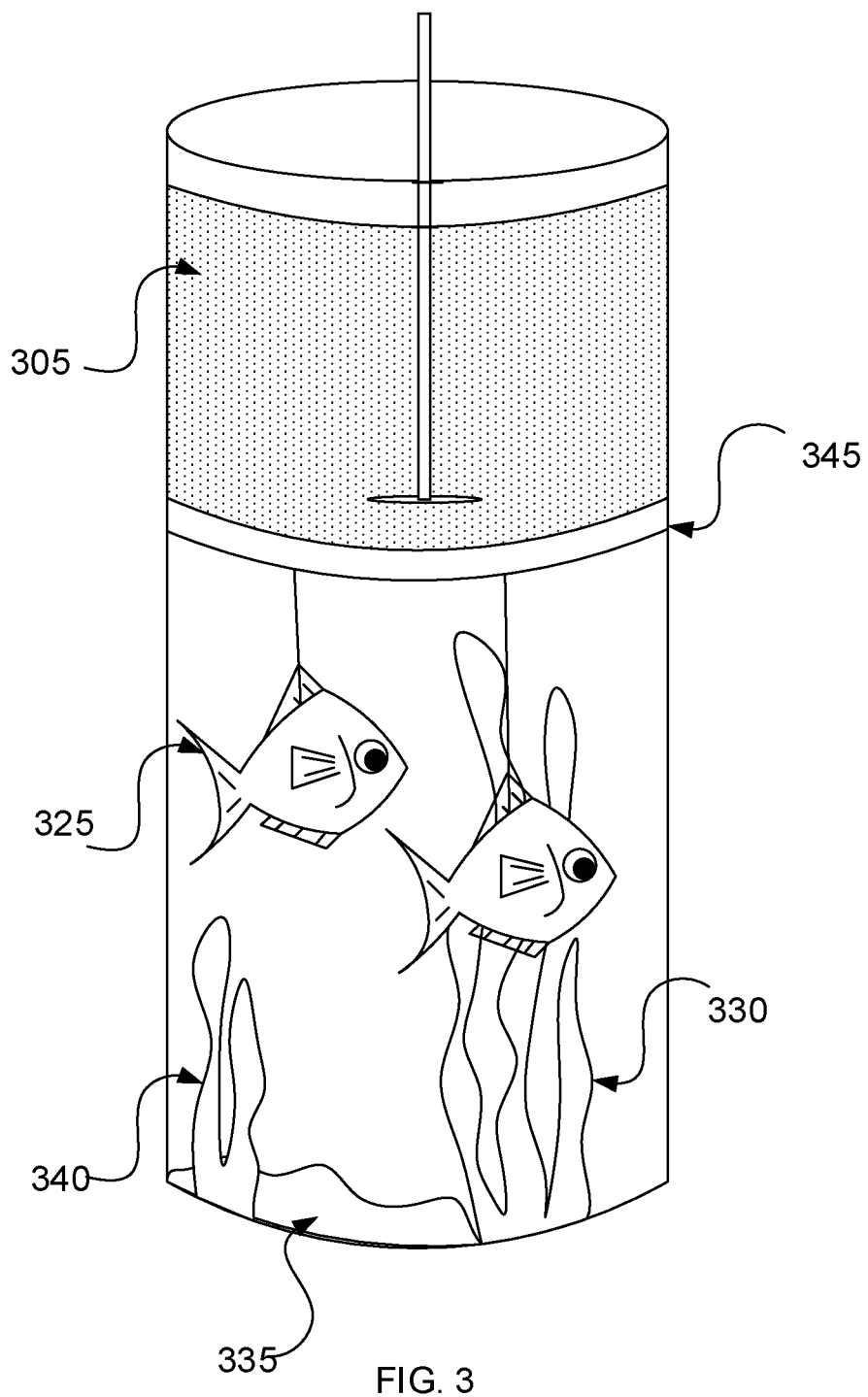
FIG. 3 illustrates an exemplary embodiment of a floating candle in a transparent cylindrical container with an anchored floating suspended decoration.

Referring now to FIG. 3, an exemplary embodiment of a floating candle 305 in a transparent cylindrical container 300 with an anchored floating suspended decoration 325, 330 is illustrated. In some aspects, the floating candle 305 may comprise an air freshener, wherein the floating candle 305 may not be configured to melt, and accordingly may not require a wick. In some aspects, bubbles may be deliberately caused to give a bubble effect to the floating candle 305. For example, as illustrated, bubbles in the floating candle 305 may fit with the underwater motif.

In some embodiments, the suspension base 320 may comprise a mixture of suspended decorations 325, 330, 335, including, for example, top-anchored floating suspended decorations 325, bottom-anchored floating suspended decorations 330, and static suspended decorations 335. A top-anchored floating suspended decoration 325 may be denser than the suspension material, wherein the anchoring may prevent the top-anchored floating suspended decoration 325 from sinking. In some aspects, the top-anchored floating suspended decoration 325 may be anchored by a string that may allow for some swinging movement. In some implementations, a barrier layer 345 may be located between the floating candle 305 and the suspension base 325. The barrier layer 345 may seal in the suspension material, limiting leakage, particularly where the suspension material may comprise a fluid. In some aspects, the barrier layer 345 may provide a sturdy anchor point for a top-anchored floating suspended decoration 325 or a wick base.

In some embodiments, a bottom-anchored floating suspended decoration 330 may be directly anchored to a surface of the cylindrical container 300, wherein the bottom-anchored floating suspended decoration 330 may be more buoyant than the suspension material. In some implementations, the bottom-anchored floating suspended decoration 330 may be partially anchored to a surface, allowing a portion to float up with some swinging movement. In some implementations, static suspended decorations 335 may be integrated into a partially anchored scene, and exterior decorations 340 may further enhance the aesthetic.

For example, as illustrated, the top-anchored floating suspended decoration 325 may comprise fish hanging by a transparent filament extending from the barrier layer 345, and static suspended decorations 335 may comprise sand and coral to simulate the ocean floor. The bottom-anchored floating suspended decoration 330 may comprise floating seaweed anchored to the bottom surface of the suspension base 320, which may be enhanced by similar seaweed painted as an exterior decoration 340, which may provide depth within the scenery.

Figure 4:
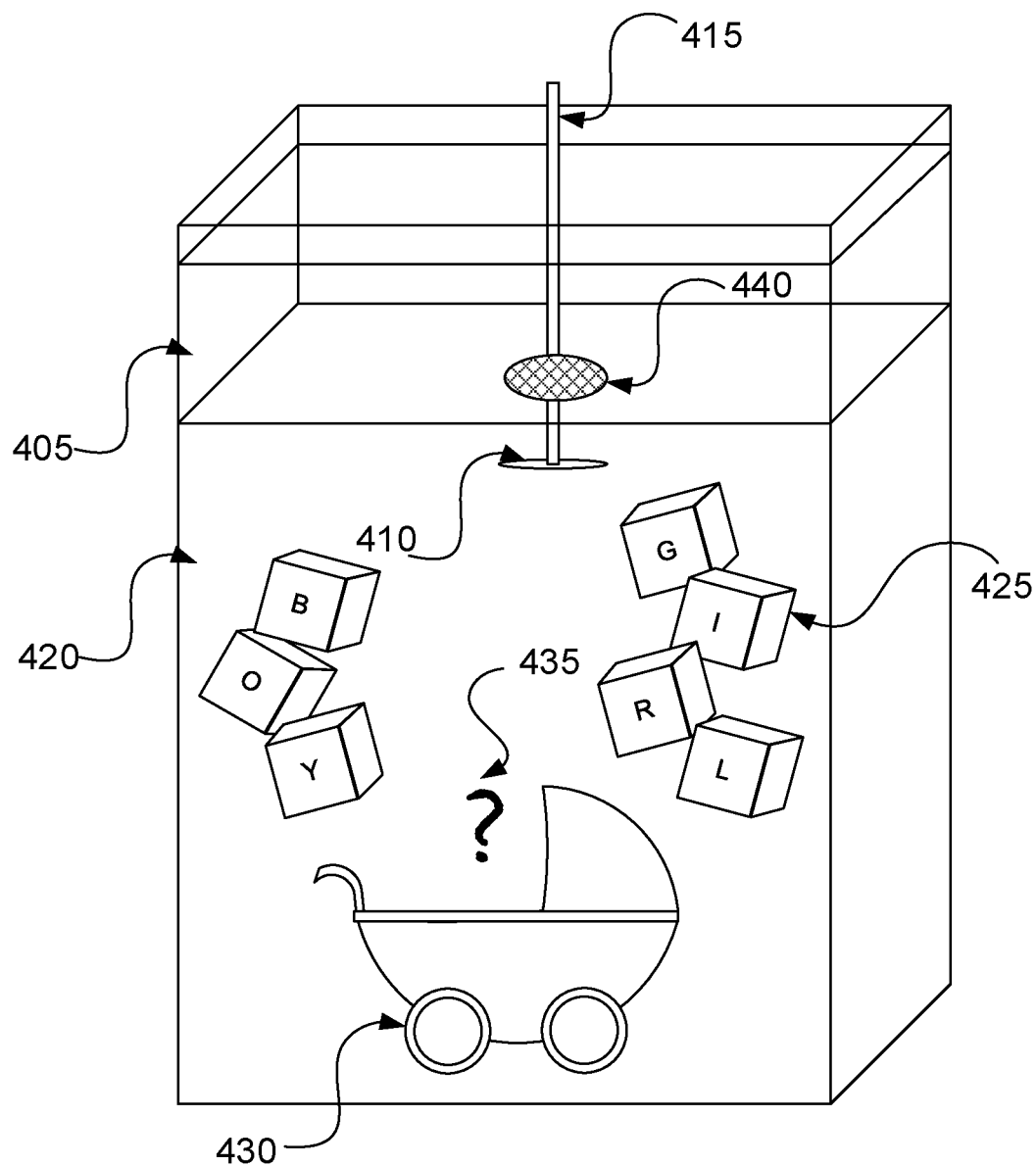
FIG. 4 illustrates an exemplary embodiment of a floating candle in a transparent cuboid container, wherein the floating candle may change colors during use.

Referring now to FIG. 4, an exemplary embodiment of a floating candle 405 in a transparent cuboid container 400, wherein the floating candle may change colors during use is illustrated. In some implementations, the suspension base 420 may comprise floating suspended decorations 425, external decorations 435, and static suspension decorations 430. In some aspects, the floating candle 405 may comprise a wick 415 with wick base 410 that may interact with a color pocket 440, wherein burning the wick 415 may cause the color pocket 440 to pop or bleed. In some embodiments, the color pocket 440 may comprise a dye or a colored wax that may tint material it comes in contact with, such as one or both the candle material and the suspension material. In some implementations, the wick 415 may be dipped in color and coated to hide a reveal. In some aspects, a different core color may be used for the reveal, which would feed into the suspension base 420 to slowly change its color. In some embodiments, a core may be replaced and reused. In some implementations, a suspension base 420 may be re-treated to return it to its original color so that it may be reused.

As an illustrative example, as shown, the floating candle 405 may be used in a baby's gender reveal event, wherein the color pocket 440 may comprise a blue or a pink fluid or wax. The decorations 425, 430, 435 may relate to the motif of a baby shower and gender reveal. Once the color pocket 440 is pierced or melted, either pink or blue will permeate one or both the floating candle 405 or the suspension base 420 indicating the gender of the expected baby.

Figure 5:
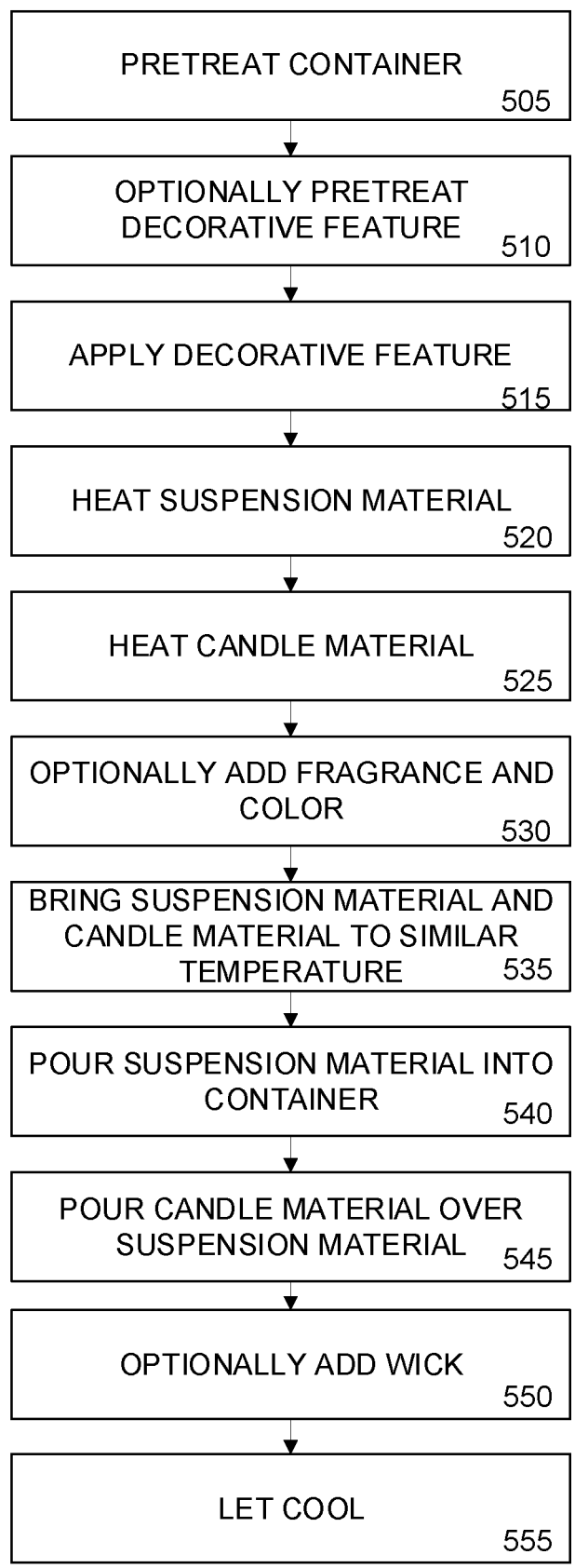
FIG. 5 illustrates exemplary method steps for floating a candle over a water base with suspended decoration.

Referring now to FIG. 5, exemplary method steps for floating a candle over a water base with suspended decoration are illustrated. In some aspects, at 505, the container may be pretreated, which may include, for example, sterilizing, cleaning, heat treatments, or other pretreatment techniques. In some embodiments, at 510, the decorative features may be pretreated. There may be different pretreatment techniques for different decorative features depending on the material and its application. For example, an exterior decorative feature may have a different pretreatment than a floating suspended decoration. The decorative feature may be heat-treated to reduce color loss over time. The decorative feature may be coated to limit damage caused by extended exposure to fluid.

At 515, the decorative features may be applied to the container. In some aspects, such as where the decorative feature will be suspended in the suspension base, the decorative feature may be anchored to a surface of the container prior to the addition of the suspension material. In some implementations, where the decorative features may have exterior decorations, the decorative features may be applied after the cooling process to limit damage to any adhesives.

At 520, the suspension material may be heated. At 525, the candle material may be heated, and in some embodiments, at 530, fragrance and color may be added to the candle material. In some aspects, the suspension material may be tinted. In some implementations, at 535, the suspension material and the candle material may be heated to the same or similar temperatures, wherein the similarity may allow the candle material to effectively float over the suspension material with limit splattering and mixing. At 540, the suspension material may be added to the container, and at 545, the wax material may be poured over the suspension material. In some aspects, the wax material may be poured onto an intermediary surface before pouring into the container to limit splattering. In some aspects, at 550, the wick may be added, and at 555, the floating candle and suspension material may cool until hardened.

In some aspects, a candle may pair with a smart device to enhance a user's functionality of the candle. In some implementations, a user may manipulate the three-dimensional environment within the candle. For example, the suspension base may contain a three-dimension cityscape where a user can manipulate and enhance or de-emphasize its three-dimensional features.

In some embodiments, a portion of the candle's housing may have electronics or lighting to highlight or enhance the decorative features of what is contained in the suspension base. In some implementations, electronics may be in the base of the candle's housing. In some aspects, electronics may be extended through the base and stem of the candle's housing. In some embodiments, light-emitting diodes may have a constant on and off loop or may be programmed by a user. In some implementations, light-emitting diodes may change color to complement the decorative features of the candle. In some aspects, light-emitting diodes may change color to enhance or highlight a color change as it happens. For example, the process described above in FIG. 4 may be paired with lighting to further accentuate when a gender reveal occurs.

In some embodiments, a power source may be replaceable or rechargeable. In some implementations, a power source may be recharged through a USB port, such as a USB-C or micro-USB port, or by conductive charging.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A floating candle device comprising:
   a suspended decoration;
   a suspension base comprising at least one suspension composition configured to house the suspended decoration;
   a floating candle located within the suspension base and above the suspension base;
   a container configured to house the suspended decoration, the suspension base, and the floating candle;
   a barrier layer located between the suspension base and the floating candle, wherein the barrier layer seals the suspension base within the container;
   a wick;
   a wick base configured to anchor the wick within the floating candle; and
   a candle material configured to melt as the wick burns, wherein the wick base is anchored in the barrier layer.

2. The floating candle device of claim 1, wherein the suspended decoration is anchored to the container.

3. The floating candle device of claim 1, wherein the suspended decoration floats within the suspension base.

4. The floating candle device of claim 1, wherein the suspended decoration comprises a first portion and a second portion, wherein the first portion floats within the suspension base and the second portion is anchored to the container.

5. The floating candle device of claim 1, wherein the suspension composition comprises a solid.

6. The floating candle device of claim 1, wherein the suspension composition comprises a fluid.

7. The floating candle device of claim 1, further comprising a surface decoration located on a surface of the container.

8. The floating candle device of claim 1, wherein one or both the floating candle or the suspension base comprises one or more colors.

9. The floating candle device of claim 1, wherein one or both the floating candle or the suspension base comprises one or more fragrances.

10. The floating candle device of claim 1, wherein the floating candle is replaceable.

11. The floating candle device of claim 1, wherein the suspended decoration comprises a first portion and a second portion, wherein the first portion floats within the suspension base and the second portion is anchored to one or both the container or the barrier layer.

12. The floating candle device of claim 1, wherein the candle material comprises a gel.

13. The floating candle device of claim 1, wherein the suspension composition comprises a gel or a fluid.

14. The floating candle device of claim 1, wherein the suspension composition comprises a solid.

* * * * *